United States Patent
Devenyi

(10) Patent No.: US 6,728,430 B1
(45) Date of Patent: Apr. 27, 2004

(54) FLUID IDENTIFICATION SYSTEM

(75) Inventor: Gabor Devenyi, Penetanguishine (CA)

(73) Assignee: Raytheon Company, Waltham, MA (US)

( * ) Notice: Subject to any disclaimer, the term of this patent is extended or adjusted under 35 U.S.C. 154(b) by 47 days.

(21) Appl. No.: 10/045,561

(22) Filed: Jan. 9, 2002

(51) Int. Cl.$^7$ .............. G02B 6/00; G01N 21/41
(52) U.S. Cl. .............. 385/12; 356/128; 356/133; 250/227.11; 250/227.14
(58) Field of Search .............. 385/12, 13; 250/227.14, 250/227.11; 356/128, 133, 73.1

(56) References Cited

U.S. PATENT DOCUMENTS

| | | | | |
|---|---|---|---|---|
| 3,513,319 A | * | 5/1970 | Broerman | 250/576 |
| 3,933,409 A | * | 1/1976 | Kloots | 385/45 |
| 4,240,747 A | * | 12/1980 | Harmer | 356/133 |
| 4,287,427 A | * | 9/1981 | Scifres | 250/577 |
| 4,427,293 A | * | 1/1984 | Harmer | 356/133 |
| 4,564,292 A | * | 1/1986 | Omet | 356/133 |
| 4,851,817 A | * | 7/1989 | Brossia et al. | 340/583 |
| 4,942,306 A | * | 7/1990 | Colbourne | 250/577 |
| 4,950,885 A | * | 8/1990 | Kershaw | 250/227.25 |
| 4,994,682 A | * | 2/1991 | Woodside | 250/577 |
| 5,005,005 A | * | 4/1991 | Brossia et al. | 340/604 |
| 5,253,037 A | * | 10/1993 | Klainer et al. | 356/133 |
| 5,384,871 A | | 1/1995 | Devenyi | 385/19 |
| 5,995,686 A | * | 11/1999 | Hamburger et al. | 385/12 |

* cited by examiner

Primary Examiner—Hemang Sanghavi
Assistant Examiner—Scott Knauss
(74) Attorney, Agent, or Firm—William C. Schubert; Glenn H. Lenzen, Jr.

(57) ABSTRACT

A fluid detector system for identifying a fluid or detecting presence of a substance in a fluid. The fluid detector includes at least two optical conductors, optical detectors coupled to outputs from the optical conductors; and a comparer for comparing the outputs from the detectors. Each optical conductor has an outer reflective surface. A first one of the optical conductors has a section with at least a portion of its outer reflective surface removed. The comparer can determine an optical refraction index of fluid at the section of the first optical conductor which has the portion of the outer reflective surface removed.

17 Claims, 2 Drawing Sheets

FLUID IDENTIFICATION SYSTEM

BACKGROUND OF THE INVENTION

1. Field of the Invention

The present invention relates to detecting in fluids and, more particularly, to a fluid detector which uses optical conductors and reflectance of fluids to obtain measurements.

2. Prior Art

U.S. Pat. No. 5,384,871 discloses a fiber optic coupling and measurement apparatus using a flexible liquid filled bladder. Various different physical and electrical systems are known for detecting, selecting or verifying the presence or absence of fluids, liquids or components in fluids and liquids. However, there is a desire for a new type of detecting system which preferably has no moving parts and no electrical contact with the fluids or liquids.

SUMMARY OF THE INVENTION

In accordance with one aspect of the present invention, a fluid detector system is provided for identifying a fluid or detecting presence of a substance in a fluid. The fluid detector includes at least two optical conductors, optical detectors coupled to outputs from the optical conductors; and a comparer for comparing the outputs from the detectors. Each optical conductor has an outer reflective surface. A first one of the optical conductors has a section with at least a portion of its outer reflective surface removed. The comparer can determine an optical refraction index of fluid at the section of the first optical conductor which has the portion of the outer reflective surface removed.

In accordance with another aspect of the present invention, a fluid detector is provided comprising a light source; at least two main light conductors coupled to the light source by a branching light conductor; a fluid container having the first light conductor extending therethrough; and optical sensors couple to ends of the main light conductors for separately sensing light transmissions from the light source through the main light conductors. A first one of the light conductors has an outer lateral side having a section without a reflective surface. The outer side section without the reflective surface is located in the fluid container.

In accordance with one method of the present invention, a method of determining a fluid or presence of a substance in a fluid is provided comprising steps of transmitting optical energy into two optical conductors, a first one of the optical conductors having a side section without a reflective outer surface; reflecting optical energy at the side section back into the first optical conductor by fluid located against the first optical conductor at the side section; and comparing transmission levels of the optical energy transmitted through the two optical conductors.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENT

Figure 1:
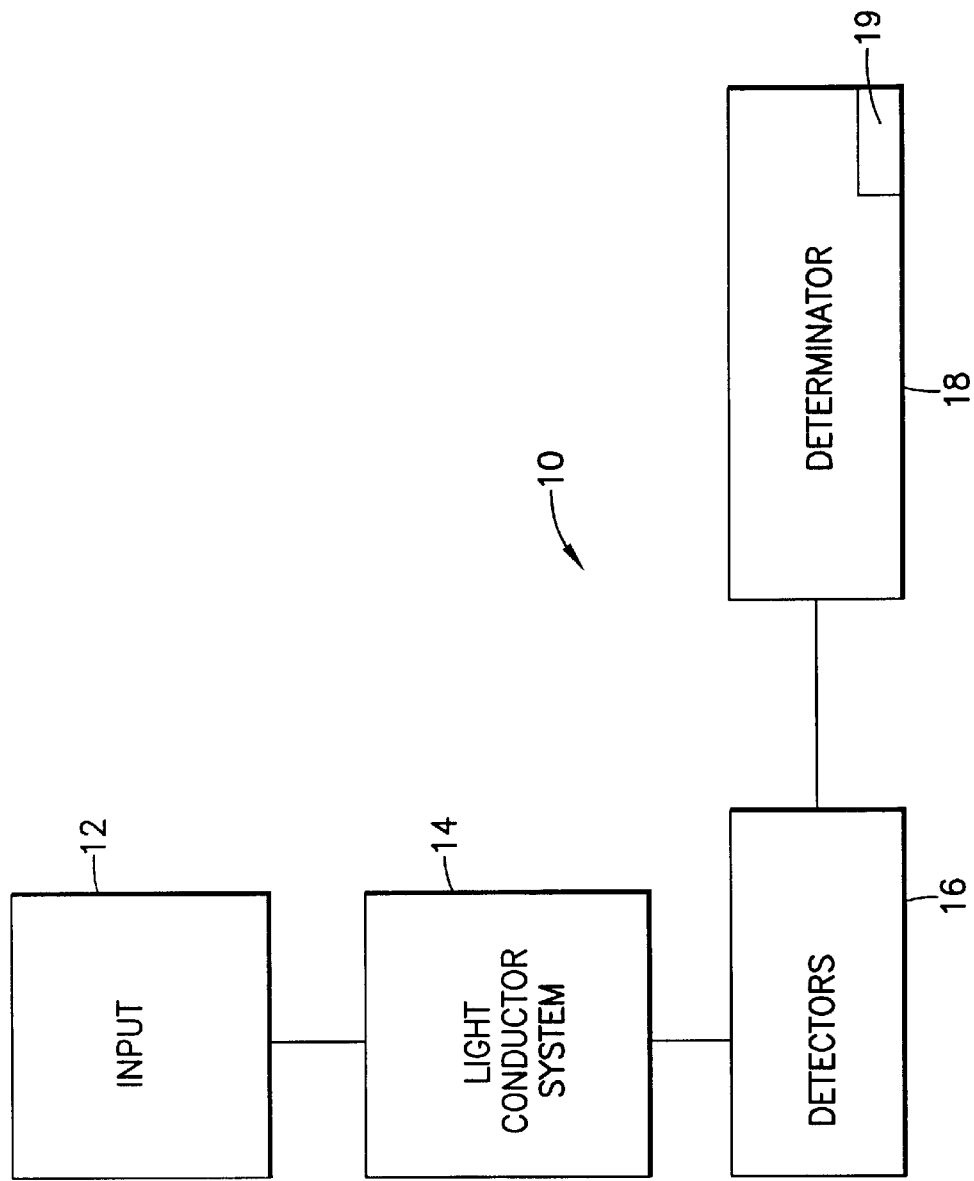
FIG. 1 is a block diagram of components in a system comprising features of the present invention.

Referring to FIG. 1, there is shown a block diagram of a detector system 10 incorporating features of the present invention. Although the present invention will be described with reference to the single embodiment shown in the drawings, it should be understood that the present invention can be embodied in many alternate forms of embodiments. In addition, any suitable size, shape or type of elements or materials could be used.

The detector system 10 generally comprises an optical energy source or input 12, a light conductor system 14, detectors 16, and a determinator 18. The energy source or input 12 could comprise any suitable type of light source, such as an LED. In a preferred embodiment, the input 12 comprises a single light source. However, in alternate embodiments, the input 12 could comprise multiple light sources.

The input 12 is coupled to an input end of the light conductor system 14. The detectors 16 are coupled to an output end of the light conductor system 14. In a preferred embodiment, the detectors 16 comprise multiple optical detectors. However, in an alternate embodiment, the detectors 16 could comprise a single optical detector functionally split into two or more separate sections.

The determinator 18 is connected to outputs from the detectors 16. The determinator 18 could comprise a computer, such as comprising a memory 19 and a processor. The determinator 18 is generally adapted to compare at least two electrical signals sent from the detectors 16. The determinator 18 preferably has a user interface, such as a display, for a user to view a result of the comparison of the signals from the detectors. The memory could be preprogrammed with predetermined data of optical refraction indexes of liquids reflected into a light conductor as further understood from the description below. Alternatively, or additionally, the determinator 18 could comprise an algorithm as further understood below.

Figure 2:
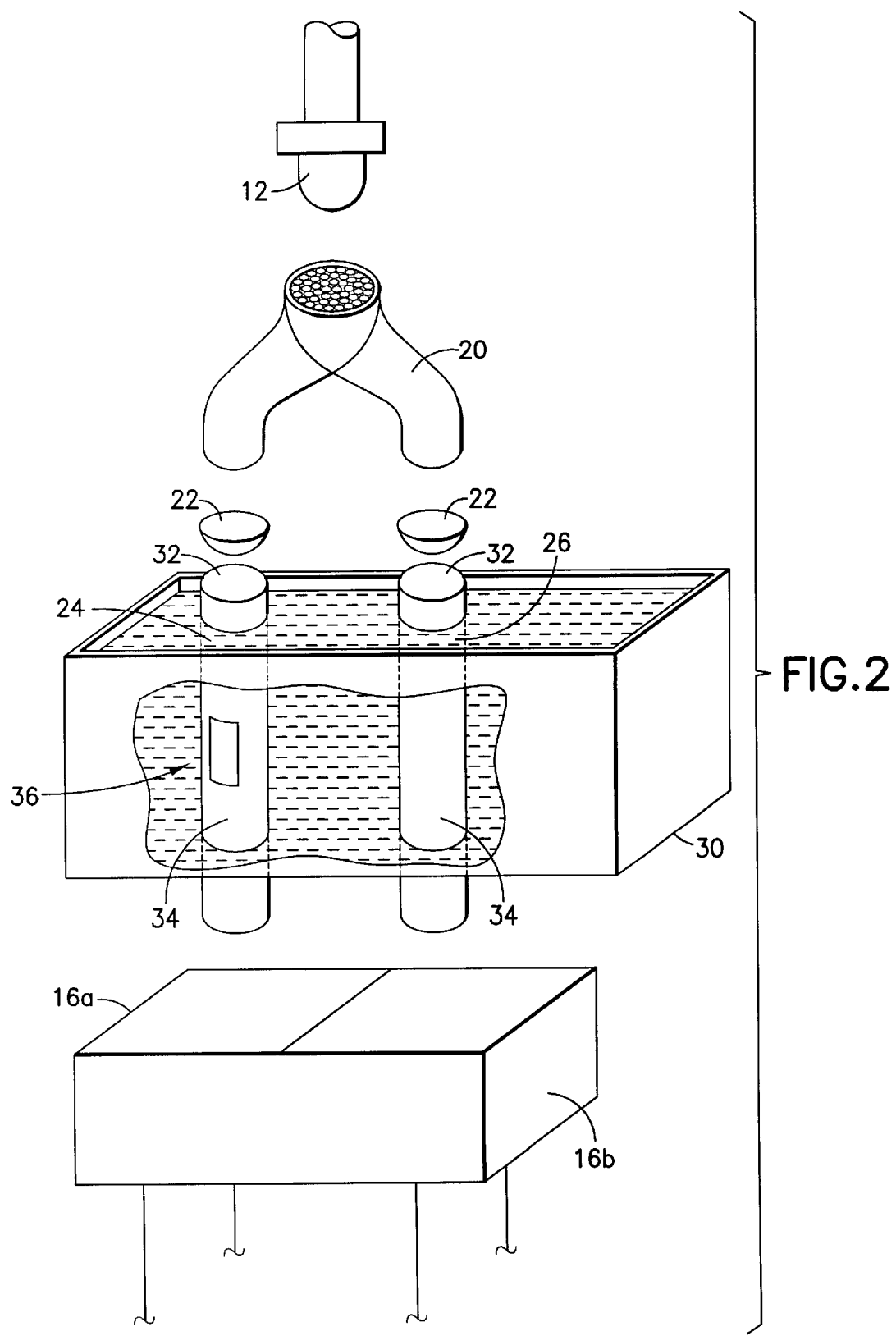
FIG. 2 is an exploded perspective view of components of the system shown in FIG. 1.

Referring also to FIG. 2, the light conductor system 14 generally comprises a bifurcated optical fiber bundle 20, collimator lenses 22, and optical conductors 24, 26. In a preferred embodiment, the optical conductors 24, 26 extends through a fluid container 30. However, in alternate embodiments, the second optical conductor 26 might not extend through the fluid container 30. In another alternate embodiment of the present invention, the fluid container 30 might not be provided, such as when the optical conductors 24, 26 are suitably shaped to be extended or inserted into a container, or are for sensing environmental gas(es).

The bifurcated optical fiber bundle 20 forms a branched optical conductor between the light source 12 and first ends of the main optical conductors 24, 26. In an alternate embodiment, the optical fiber bundle 20 could comprise any suitable number of branches. In another alternate embodiment, any suitable type of branching light conductor could be provided. In another alternate embodiment, the bifurcated optical fiber bundle 20 might not be provided, such as when there are a plurality of light sources; one for each main optical conductor.

In the embodiment shown, collimator lenses 22 are provided between the bifurcated optical fiber bundle 20 and input ends of the main optical conductors 24, 26. However, in an alternate embodiment, the collimator lenses might not be provided.

In the embodiment shown, the system has two main optical conductors 24, 26. However, in alternate embodiments, the system could comprise more than two main optical conductors. In the embodiment shown, the two main optical conductors 24, 26 are substantially identical to each other with one exception as further explained below. In the embodiment shown, the two main optical conductors 24, 26 are preferably optical fibers. Each fiber comprises a fiber core 32 and an outer cladding or reflective surface 34. In an alternate embodiment, the optical conductors 24, 26 might comprise any suitable type of optical conductor, such as a light pipe.

The first optical conductor 24 differs from the second optical conductor 26 in that a side portion or section 36 of its of reflective outer surface 34 has been removed. In an alternate embodiment, the first optical conductor 24 could be initially formed without the portion 36. The section 36 could be formed by any suitable means to form a reflective discontinuity, such as notching, grooving or scoring the outer reflective surface of the first optical conductor. The section 36 could comprise any suitable type of shape, such as an annular groove. In the embodiment shown, the first optical conductor 24 has only one section 36. However, in alternate embodiments, the first optical conductor 24 could comprise multiple sections 36, perhaps in regular calibrated intervals along its length. The side section 36 is located inside the container 30. Thus, when fluid or liquid is inserted into the container 30, the fluid or liquid is located directly against the fiber core 32 at the open side section 36.

In the embodiment shown, the two optical conductors 24, 26 extend between opposite sides of the container 30. However, in an alternate embodiment, one or both of the optical conductors 24, 26 could extend through any suitable sides. In one type of alternate embodiment, one or both of the optical conductors 24, 26 could have a general loop shape to extend into and out of the container from a same side. In another alternate embodiment, one or both of the optical conductors could terminate in the container 30 and have a reflective end with a 50/50 beam splitter and both the input and photo detector at its input end. In this type of alternate embodiment, the optical conductor could comprise a conical rod with one or more annular notches to remove the reflective outer cladding.

The bifurcated optical fiber bundle 20 is adapted to provide equal amounts of light or optical energy to the two main optical conductors 24, 26. The second optical conductor 26 is used to produce a "baseline" output from the second detector 16b to the determinator 18. The first detector 16a, because the portion 36 of the first optical conductor's outer reflective surface has been removed, will have a lower electrical output than the second detector 16b. However, the output from the first detector 16a will vary depending upon the optical refraction index of the fluid located at the side section 36.

The present invention is adapted to use different optical refraction indices of different fluids in order to determine or detect fluids or substances in fluids. The lower the optical refraction index of the fluid, the larger the electrical output from the first detector 16a. This is due to the fact that the fiber optic core has a higher index optical material then the cladding material. The cladding of the fiber acts like a reflector to the core which is a high index optical conductor.

By removing a portion of the cladding, the total internal reflection of the fiber optic stand is reduced. By effectively reestablishing the reflectiveness of the missing cladding through the liquid contact, reflectiveness can be nearly restored. In general, the higher the difference between the optical index of the core and the optical index of the cladding, the better the efficiency of the light transmission. Of course, the efficiency is also affected by the initial wavelength of the light source, numerical aperture, etc. In fact, if the liquid is a high index material, similar to the core index or higher of the fiberoptic conductor, the loss within the fiber will be larger than original clad fiberoptic conductor due to the fact that some of the light will be bled or conducted into the liquid in contact with the fiber rather than reflected back into the core and, thereby reducing the output of the fiber to the detector. The higher the optical refraction index of the fluid, the lower the electrical output from the first detector 16a. The electrical signal output from the first detector 16a is compared to the electrical output from the second detector 16b to determine the optical refraction index of the fluid. Based upon this determination, the determinator 18 can determine the type of fluid or substances in the fluid, based upon information stored in the memory 19.

The present invention provides a fluid detector which consists of a light source or optical energy source shared by two lengths of optical fiber. A first one of the optical fibers is provided with a notch or discontinuity (removing some of the cladding or reflective surface), and thereby reducing the light transmission efficiency of the fiber. A second one of the optical fibers is not provided with this notch or discontinuity in its cladding or reflective surface. The free ends of the fibers are coupled to light sensors whose output is monitored. As the liquid comes into contact with the optical fibers, the light transmission levels in the notched optical fiber will increase; as long as the optical refraction index of the liquid is lower than the optical refraction index of the fiber core. The increased optical transmission induces a higher electrical output in the photocell coupled to the fiber, registered, and compared with the baseline optical fiber output providing comparative data.

The present invention can provide a purely optical means of detecting, selecting or verifying the presence of several fluids or liquids, due to the different refraction indices of each liquid, that is being detected. It is possible that this type of sensor could be used to detect contamination, salt content and other impurities. The present invention could be useful for non-clear liquids by employing the appropriate wavelength of optical energy source, optical conductor, and sensors. By providing a baseline light or energy output through a standard optical fiber or optical conductor, and comparing it with a variable internal reflection optical fiber, different fluids with different optical refraction indices can be sensed and detected.

The present invention can be used with no moving parts. The present invention can be used with no electrical contact with the fluids or liquids. The present invention can be optimized for the media being sensed. The present invention can provide time based sampling which can be made by pulsing the optical energy source to the fibers. The present invention can provide a relatively simple, but highly reliable detector.

In an alternate embodiment, the system might only comprise a single main optical conductor with a portion of its outer reflective surface removed; without the "baseline" second optical conductor. In this alternate embodiment, the system might comprise only a single optical detector. In this alternate embodiment, the memory 19 might comprise "baseline" optical transmission data that can be compared by the signal processor of the determinator 18 to the signal received from the optical detector. The signal processor might also comprise an algorithm, bases upon predetermined data or measurements, for identifying a fluid based upon a signal from the optical detector, or identifying a component or quantity of a component in a fluid.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A fluid detector system for identifying a fluid or detecting presence of a substance in a fluid, the fluid detector comprising:

at least two optical conductors, each optical conductor having an outer reflective surface, a first one of the optical conductors having a section with at least a portion of its outer reflective surface removed, a second one of the optical conductors not having its outer reflective surface removed except at ends of said second optical conductor;

optical detectors coupled to outputs from the optical conductors; and means for comparing the outputs from the detectors to determine an optical refraction index of fluid at the section of the first optical conductor which has the portion of the outer reflective surface removed.

2. A fluid detector system as in claim 1 wherein the optical conductors comprise fiber optic members.

3. A fluid detector system as in claim 2 wherein the portion comprises cladding removed from an outside surface of the fiber optic member which forms the first optical conductor.

4. A fluid detector system as in claim 1 wherein the optical conductors comprise light pipes.

5. A fluid detector system as in claim 1 wherein the two optical conductors are substantially identical to each other except for the first optical conductor having a portion of its outer reflective surface removed.

6. A fluid detector system as in claim 1 further comprising a branched optical fiber bundle located between the optical conductors and a light source.

7. An optical detector system as in claim 6 further comprising collimator lenses between the branched optical fiber bundle and ends of the two optical conductors.

8. An optical detector system as in claim 1 further comprising a container for containing the fluid, wherein the first optical conductor extends through the container.

9. A fluid detector comprising:

a light source;

at least two main light conductors coupled to the light source by a branching light conductor, a first one of the light conductors having an outer side section without a reflective surface, a second one of the optical conductors not having its outer reflective surface removed except at ends of said second optical conductor;

a fluid container having the first light conductor extending therethrough, the outer side section without the reflective surface being located in the fluid container;

optical sensors couple to ends of the main light conductors for separately sensing light transmissions from the light source through the main light conductor; and a system for comparing output signals from the optical sensors to determine an optical refraction index of fluid at the section of the first optical conductor which has the portion of the outer reflective surface removed.

10. A fluid detector as in claim 9 wherein the main light conductors comprise fiber optic members.

11. A fluid detector as in claim 10 wherein the outer side section without a reflective surface comprises a portion of cladding of a first one of the fiber optic members being removed to expose a core of the optical member.

12. A fluid detector as in claim 9 wherein the branching light conductor comprises a bifurcated optical fiber bundle.

13. A fluid detector as in claim 9 wherein the system for comparing comprises a determinator for comparing the output signals of the optical sensors to each other.

14. A fluid detector as in claim 13 further comprising collimator lenses located between the bifurcated optical fiber bundle and the main light conductors.

15. A method of determining a fluid or presence of a substance in a fluid comprising steps of:

transmitting optical energy into two optical conductors, a first one of the optical conductors having a lateral side which has a section without a reflective outer surface, a second one of the optical conductors not having its outer reflective surface removed except at ends of said second optical conductor;

reflecting optical energy at the section back into the first optical conductor by fluid located against the section; and comparing transmission levels of the optical energy transmitted through the two optical conductors to determine an optical retraction index of the fluid at the section of the lateral side of the first optical conductor without a reflective outer surface.

16. A method as in claim 15 is wherein the step of transmitting optical energy into the two optical conductors comprises separating the optical energy into two components from a single light source.

17. A method as in claim 15 wherein the step of reflecting optical energy at the side section varies the amount of optical energy reflected back into the first optical conductor by the fluid dependent upon an optical refraction index of the fluid.

* * * * *